(12) United States Patent
Soong

(10) Patent No.: US 8,741,882 B2
(45) Date of Patent: Jun. 3, 2014

(54) ANTI-DIABETIC COMPOUNDS

(75) Inventor: John Soong, Chino, CA (US)

(73) Assignee: Sen Capital, LLC., Chino, CA (US)

( * ) Notice: Subject to any disclaimer, the term of this patent is extended or adjusted under 35 U.S.C. 154(b) by 21 days.

(21) Appl. No.: 13/354,833

(22) Filed: Jan. 20, 2012

(65) Prior Publication Data

US 2013/0190280 A1    Jul. 25, 2013

(51) Int. Cl.
*A61K 31/56* (2006.01)
*C07C 9/00* (2006.01)

(52) U.S. Cl.
USPC ............................. 514/182; 552/550; 552/553

(58) Field of Classification Search
USPC .................................. 552/550, 553; 514/182
See application file for complete search history.

(56) References Cited

U.S. PATENT DOCUMENTS

| | | | | |
|---|---|---|---|---|
| 4,793,948 A * | 12/1988 | Hatono et al. | ................. | 552/550 |
| 6,992,076 B2 * | 1/2006 | Cundy et al. | ................. | 514/182 |
| 7,049,305 B2 * | 5/2006 | Cundy et al. | ................. | 514/172 |
| 7,596,235 B2 * | 9/2009 | Michiels | ................. | 381/152 |
| 7,598,235 B2 * | 10/2009 | Cundy et al. | ................. | 514/182 |
| 7,678,782 B2 * | 3/2010 | Gallop et al. | ................. | 514/182 |

* cited by examiner

*Primary Examiner* — Sabiha N Qazi
(74) *Attorney, Agent, or Firm* — WPAT P.C.; Anthony King

(57) ABSTRACT

The preset invention relates to a new oral anti-diabetic compound prepared by synthesizing a steroid and a guanide or biguanide, which is eliminated via the hepatic route, instead of the renal route, to avoid adverse effects of administering metformin in diabetic patients with renal dysfunction. A pharmaceutical composition comprising the compound of the invention and the method for treating diabetes using the compound are also provided.

11 Claims, 5 Drawing Sheets

ANTI-DIABETIC COMPOUNDS

FIELD OF THE INVENTION

The present invention relates to new anti-diabetic compounds.

BACKGROUND OF THE INVENTION

Diabetes mellitus, often simply referred to as diabetes, is a chronic disease, which occurs when the pancreas does not produce enough insulin, or when the body cannot effectively use the insulin it produces. This leads to an increased concentration of glucose in the blood (hyperglycaemia). There are three main types of diabetes:

(1) Type 1 diabetes (previously known as insulin-dependent or childhood-onset diabetes), characterized by a lack of insulin production;

(2) Type 2 diabetes (formerly called non-insulin-dependent or adult-onset diabetes), which is caused by the body's ineffective use of insulin, and often results from excess body weight and physical inactivity; and (3) Gestational diabetes, which is hyperglycemia that is first recognized during pregnancy.

Normally, anti-diabetic drugs, which treat diabetes mellitus by lowering glucose levels in the blood, are administered orally and are thus also called oral hypoglycemic agents or oral antihyperglycemic agents. As of 2010, there are only two oral anti-diabetics in the World Health Organization Model List of Essential Medicines: Metformin and Glibenclamide [*WHO Model List of Essential Medicines,* 16th edition, World Health Organization, p. 24; December 2010].

Metformin, originally sold as Glucophage, is an oral antidiabetic drug in the biguanide class. It is the first-line drug of choice for the treatment of type 2 diabetes [*Diabetes Care.* 2009; 32 Suppl 1:S13-61]. Metformin is the only antidiabetic drug that has been conclusively shown to prevent the cardiovascular complications of diabetes. It helps reduce LDL cholesterol and triglyceride levels, and is not associated with weight gain. Metformin decreases hepatic glucose production, decreases intestinal absorption of glucose, and improves insulin sensitivity by increasing peripheral glucose uptake and utilization. With Metformin therapy, insulin secretion remains unchanged while fasting insulin levels and day-long plasma insulin response may actually decrease. However, Metformin is contraindicated in patients with renal disease or renal dysfunction. A long-term accumulation of Metformin may result in renal dysfunction.

It is desirable to develop new anti-diabetic drugs without contraindication.

SUMMARY OF THE INVENTION

The present invention relates to a new anti-diabetic compound, which is eliminated via the hepatic route, instead of the renal route, to avoid adverse effects of administering metformin in diabetic patients with renal dysfunction.

In one aspect, the invention provides a compound having the structure of Formula I or a pharmaceutically acceptable salt or a physiologically functional derivative thereof:

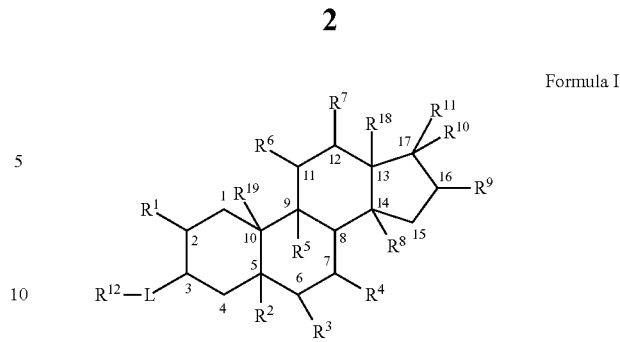

Formula I wherein $R^1$ is hydrogen, methyl, or $C_1$-$C_2$ double bond;
$R^2$ is hydrogen, bromine, chlorine, methyl, $C_4$-$C_5$ double bond, $C_5$-$C_6$ double bond, hydroxyl, or $C_5$-$C_6$ epoxy;
$R^3$ is hydrogen, bromine, chlorine, hydroxyl, methoxyl, ethoxyl, =O, —O-acetyl, or —O-benzoyl;
$R^4$ is hydrogen, hydroxyl, methoxyl, ethoxyl, =O, —O-acetyl, or —O-benzoyl;
$R^5$ is hydrogen, fluorine, $C_9$-$C_{11}$ double bond, or $C_9$-$C_{11}$ epoxy;
$R^6$ and $R^7$ are independently selected from hydrogen, hydroxyl, methoxyl, ethoxyl, =O, —O-acetyl, and —O-benzoyl;
$R^8$ is hydrogen, methyl, hydroxyl, $C_{13}$-$C_{14}$ double bond, $C_{14}$-$C_{15}$ double bond, or $C_{14}$-$C_{15}$ epoxy;
$R^9$ is hydrogen, fluorine, chlorine, bromine, iodine, hydroxyl, $C_{15}$-$C_{16}$ double bond, =O, —O-acetyl, or —O-benzoyl;
$R^{10}$ is hydrogen, halogen, hydroxyl, methoxyl, ethoxyl, =O, —O-acetyl, or —O-benzoyl, or $R^{10}$ forms a second bond between positions $C_{16}$ and $C_{17}$;
$R^{11}$ is hydrogen, methyl, ethyl, acetylenyl, vinyl, —CN, —N$_3$, carboxyl, methyl carboxyl, ethyl carboxyl, acetyl, 2-hydroxyacetyl, 1-hydroxyethyl, 1,2-dihydroxyethyl, —CHR$^{15}$—(CH$_2$)$_2$—R$^{16}$, or a lactone of the formula

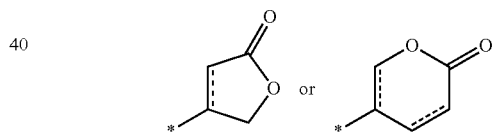

wherein the dashed bonds represent a single bond or double bond;
$R^{12}$ is a guanide or biguanide having the following formula:

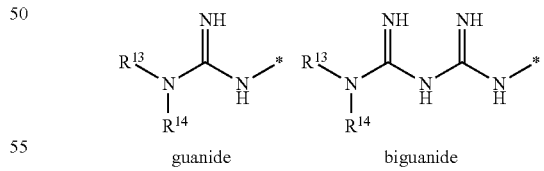

guanide          biguanide wherein $R^{13}$ and $R^{14}$ are independently selected from hydrogen, methyl, n-butyl, or phenethyl;
$R^{15}$ is hydrogen, methyl, ethyl, hydroxyl, —O-acetyl, or —O-benzoyl;
$R^{16}$ is hydrogen, iso-butyl, isocrotyl, —COOH, —COOCH$_3$, —COOCH$_2$CH$_3$, —CO—NH$_2$, —CO—NHOH, —CO—NHCH$_2$COOH, or —CO—NHCH$_2$CH$_2$SO$_3$H;
$R^{18}$ is hydrogen, methyl, or ethyl; and
$R^{19}$ is hydrogen, methyl, hydroxymethyl, formyl, carboxyl, methyl carboxyl or ethyl carboxyl; and L is COO—, a bond or a linker having 1 to 6 atoms in the main chain.

In one embodiment of the invention, the compound in free form has a structure of Formula Ia or Ib Formula Ia

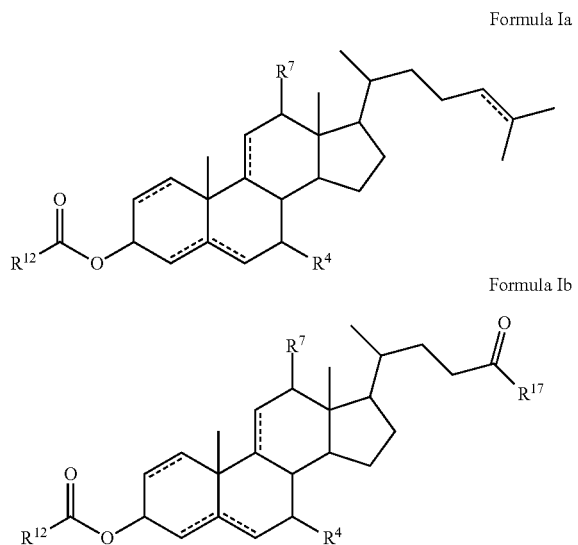

Formula Ib wherein $R^4$ and $R^7$ are independently hydrogen, hydroxyl, methoxyl, ethoxyl, =O, —O-acetyl, or —O-benzoyl;
$R^{17}$ is hydroxyl, methoxyl, ethoxyl, or one amino group selected from those of the following formulas:

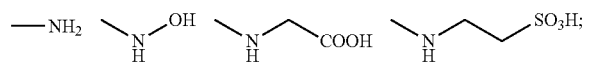

and
$R^{12}$ is a guanide or biguanide having the following formula:

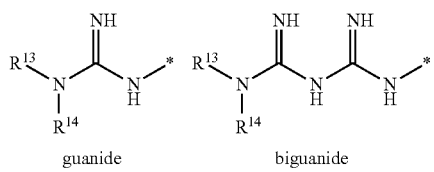

wherein $R^{13}$ and $R^{14}$ are independently selected from hydrogen, methyl, n-butyl, or phenethyl.

In another aspect, the invention provides a pharmaceutical composition comprising the compound of the invention, and a pharmaceutically acceptable salt or a physiological functional derivative thereof, which is effective in the treatment of diabetes, particularly type-2 diabetes.

In a further aspect, the invention provides a method for treating diabetes, particularly type-2 diabetes, comprising administering to a subject in need thereof a pharmaceutical composition comprising a therapeutically effective amount of the compound of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings.

DETAILED DESCRIPTION OF THE INVENTION

Figure 1:
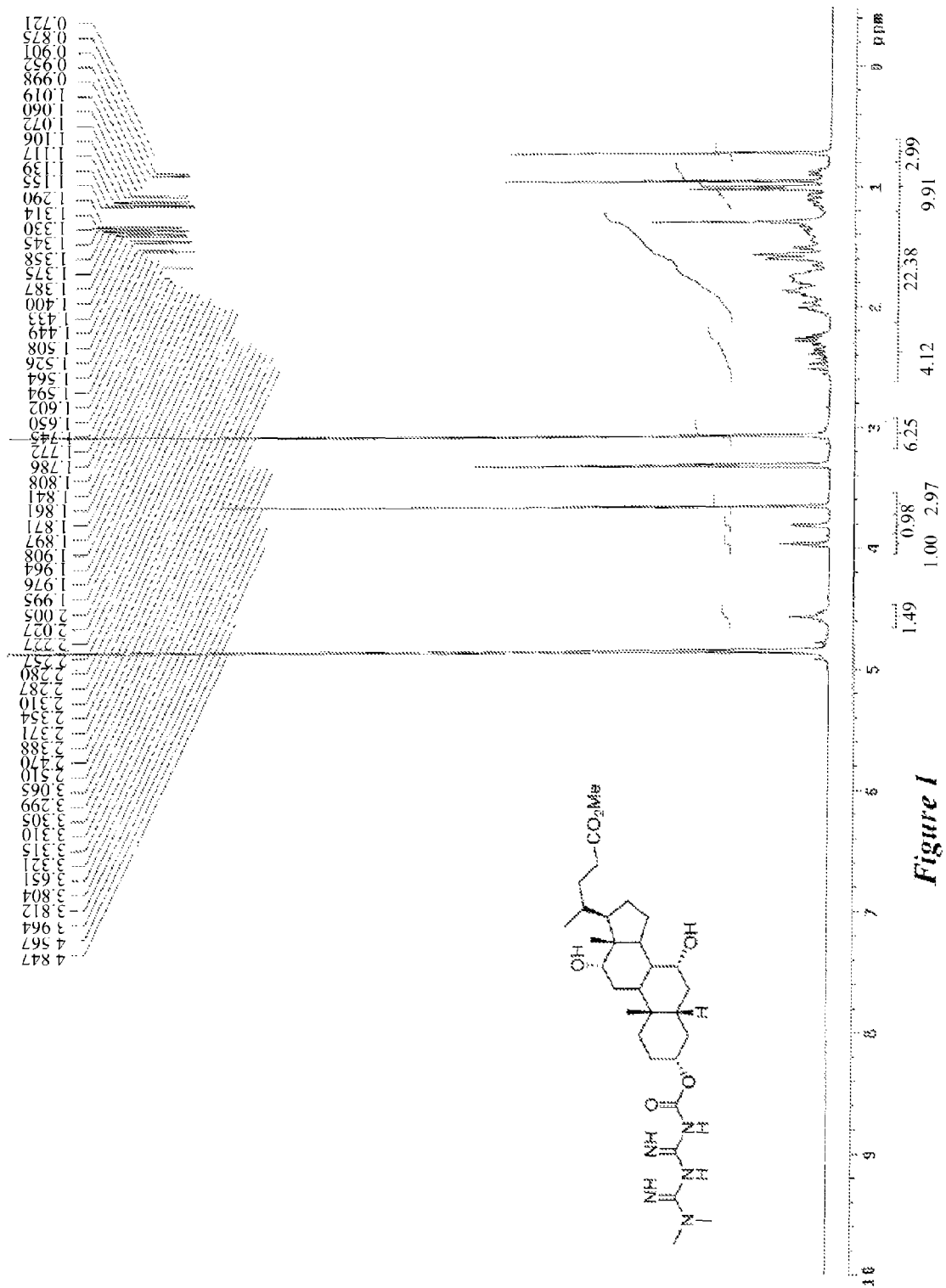
FIG. 1 provides the $^1$H NMR (CD$_3$OD, 300 Hz) profile of Compound 2, which is one example of the invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The term "Metformin" as used herein refers to N,N-dimethylimidodicarbonimidic diamide, which is first-line drug of choice for the treatment of type 2 diabetes. It has the structure below:

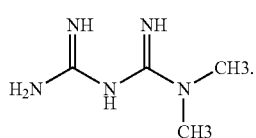

Metformin is not chemically or pharmacologically related to any other classes of oral antihyperglycemic agents. In one example of commercial products, Metformin hydrochloride USP is freely soluble in water and is practically insoluble in acetone, ether, and chloroform. The pKa of Metformin is 12.4. It is known that Metformin is excreted unchanged in the urine and does not undergo hepatic metabolism nor billary excretion. Renal clearance is approximately 3.5 times greater than creatinine clearance, which indicates that tubular secretion is the major route of Metformin elimination. Following oral administration, approximately 90% of the absorbed drug is eliminated via the renal route within the first 24 hours. In patients with decreased renal function, the plasma and blood half-life of Metformin is prolonged and the renal clearance is decreased. Accordingly, Metformin is contraindicated in patients with renal disease or renal dysfunction.

The term "steroid" as used herein refers to a compound that has a core composed of 20 carbon atoms bonded together that take the form of four fused rings as follows:

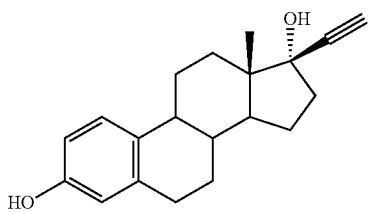 [SMILES: C#C[C@@]1(O)CCC2C3CCc4cc(O)ccc4C3CC[C@@]21C]

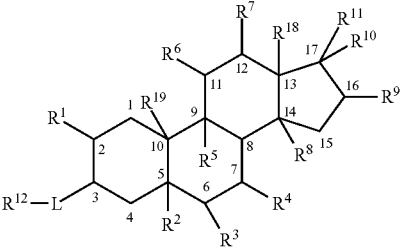
Formula I

The term "bile salt" as used herein refers to a bile acid compounded with a cation, such as sodium; which is composed of a steroid structure with four rings, a five or eight carbon side-chain terminating in a carboxylic acid, and the presence and orientation of different numbers of hydroxyl groups. Representative bile salts include the salts of taurocholic acid and glycocholic acid (derivatives of cholic acid), which represent approximately 80% of all bile salts in human. Bile salts are thought of as steroid compounds, secreted from the liver, and regarded as relatively stable and safe as compared to bile acids.

Unexpectedly, the invention provides a new oral antidiabetic drug, which is eliminated via the hepatic route, instead of the renal route, to avoid adverse effects of Metformin, such as renal dysfunction. In the invention, a new antidiabetic drug is hypothesized by a synthesis of a steroid and the two moieties below with or without a linker between them. Because a steroid including a bile salt is eliminated via the hepatic route, the compound composed of a steroid (or a bile salt) and a guanide or biguanide should be eliminated by liver. In the invention, the problem of metformin in elimination via the renal route can be solved by change the renal route to the hepatic route, so as to avoid the adverse effect of administering metformin in diabetic patients with renal dysfunction. Using a bile salt as an example, the hypothesis is illustrated below:

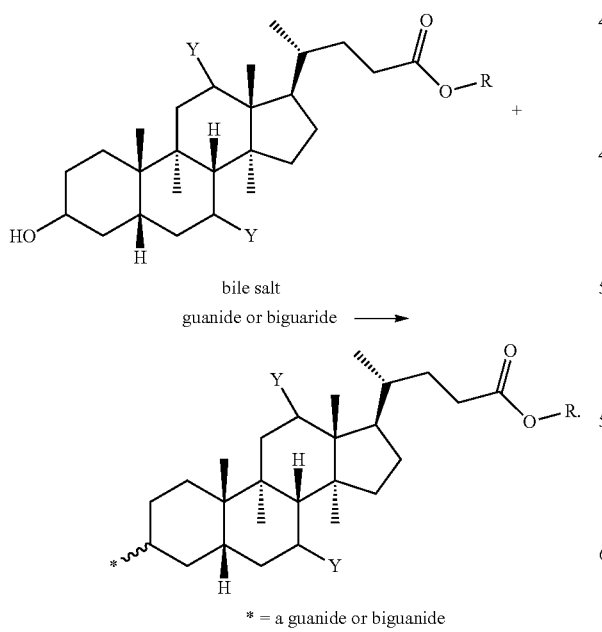

Accordingly, the invention provides a compound having the structure of Formula I or a pharmaceutically acceptable salt or a physiologically functional derivative thereof:

wherein $R^1$ is hydrogen, methyl, or $C_1$-$C_2$ double bond;

$R^2$ is hydrogen, bromine, chlorine, methyl, $C_4$-$C_5$ double bond, $C_5$-$C_6$ double bond, hydroxyl, or $C_5$-$C_6$ epoxy;

$R^3$ is hydrogen, bromine, chlorine, hydroxyl, methoxyl, ethoxyl, =O, —O-acetyl, or —O-benzoyl;

$R^4$ is hydrogen, hydroxyl, methoxyl, ethoxyl, =O, —O-acetyl, or —O-benzoyl;

$R^5$ is hydrogen, fluorine, $C_9$-$C_{11}$ double bond, or $C_9$-$C_{11}$ epoxy;

$R^6$ and $R^7$ are independently selected from hydrogen, hydroxyl, methoxyl, ethoxyl, =O, —O-acetyl, or —O-benzoyl;

$R^8$ is hydrogen, methyl, hydroxyl, $C_{13}$-$C_{14}$ double bond, $C_{14}$-$C_{15}$ double bond, or $C_{14}$-$C_{15}$ epoxy;

$R^9$ is hydrogen, fluorine, chlorine, bromine, iodine, hydroxyl, $C_{15}$-$C_{16}$ double bond, =O, —O-acetyl, or —O-benzoyl;

$R^{10}$ is hydrogen, halogen, hydroxyl, methoxyl, ethoxyl, =O, —O-acetyl, or —O-benzoyl or $R^{10}$ forms a second bond between positions $C_{16}$ and $C_{17}$;

$R^{11}$ is hydrogen, methyl, ethyl, acetylenyl, vinyl, —CN, —N$_3$, carboxyl, methyl carboxyl, ethyl carboxyl, acetyl, 2-hydroxyacetyl, 1-hydroxyethyl, 1,2-dihydroxyethyl, —CHR$^{15}$—(CH$_2$)$_2$—R$^{16}$, or a lactone of the formula

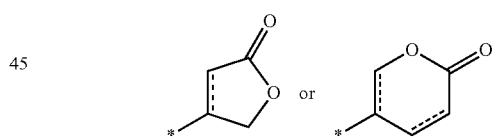

wherein the dashed bonds represent a single bond or double bond;

$R^{12}$ is a guanide or biguanide having the following formula:

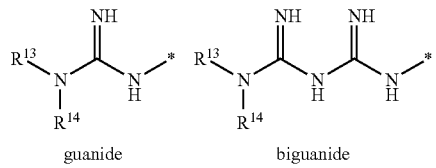

wherein $R^{13}$ and $R^{14}$ are independently selected from hydrogen, methyl, n-butyl, or phenethyl.

$R^{15}$ is hydrogen, methyl, ethyl, hydroxyl, —O-acetyl, or —O-benzoyl;

$R^{16}$ is hydrogen, iso-butyl, isocrotyl, —COOH, —COOCH$_3$, —COOCH$_2$CH$_3$, —CO—NH$_2$, CO—NHOH, —CO—NHCH$_2$COOH, or —CO—NHCH$_2$CH$_2$SO$_3$H;

$R^{18}$ is hydrogen, methyl, or ethyl; and $R^{19}$ is hydrogen, methyl, hydroxymethyl, formyl, carboxyl, methyl carboxyl or ethyl carboxyl; and L is COO—, a bond or a linker having 1 to 6 atoms in the main chain.

In one embodiment of the invention, the compound of the invention is composed of a guanide or biguanide and a bile salt, which in free form has a structure of Formula Ia or Ib below:

Formula Ia

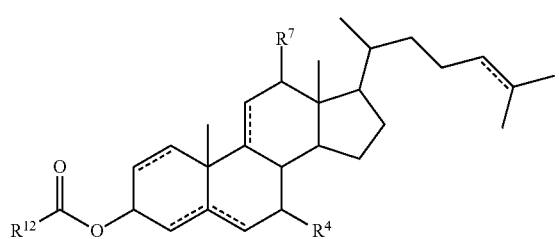

Formula Ib

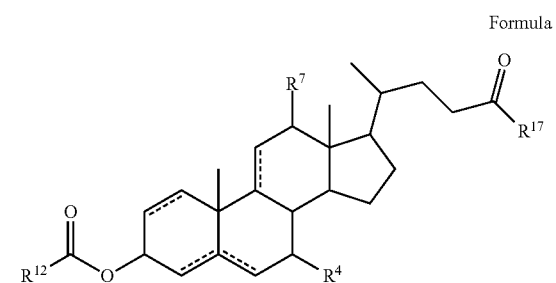

wherein $R^4$ and $R^7$ are independently hydrogen, hydroxyl, methoxyl, ethoxyl, =O, —O-acetyl, or —O-benzoyl;

$R^{17}$ is hydroxyl, methoxyl, ethoxyl, or one amino group selected from those of the following formulas:

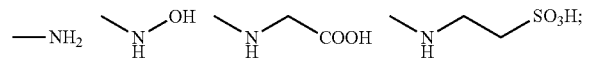

and $R^{12}$ is a guanide or biguanide having the following formula:

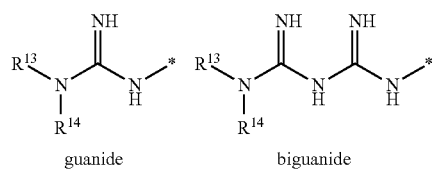

guanide    biguanide wherein $R^{13}$ and $R^{14}$ are independently selected from hydrogen, methyl, n-butyl, or phenethyl.

In one example of the invention, the guanide is

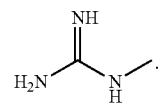

In another example of the invention, the biguanide is

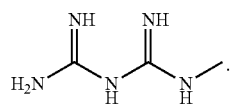

According to the invention, the compound of the invention is the structure of compound 2 below:

compound 2

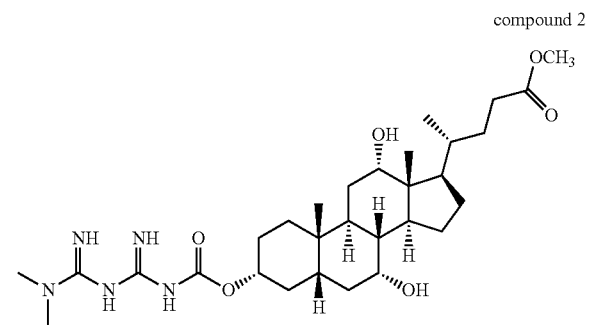

The scheme for synthesizing compound 2 is given below:

Step 1:

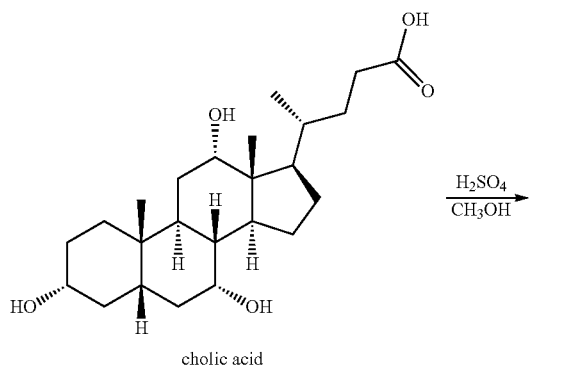

cholic acid

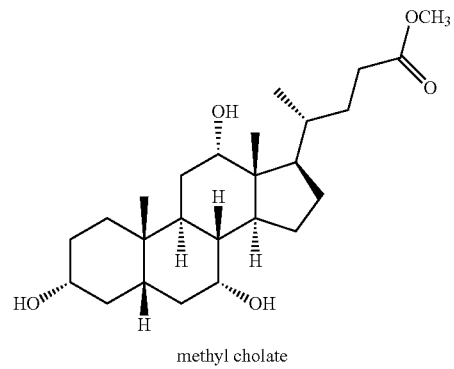

methyl cholate

Step 2:
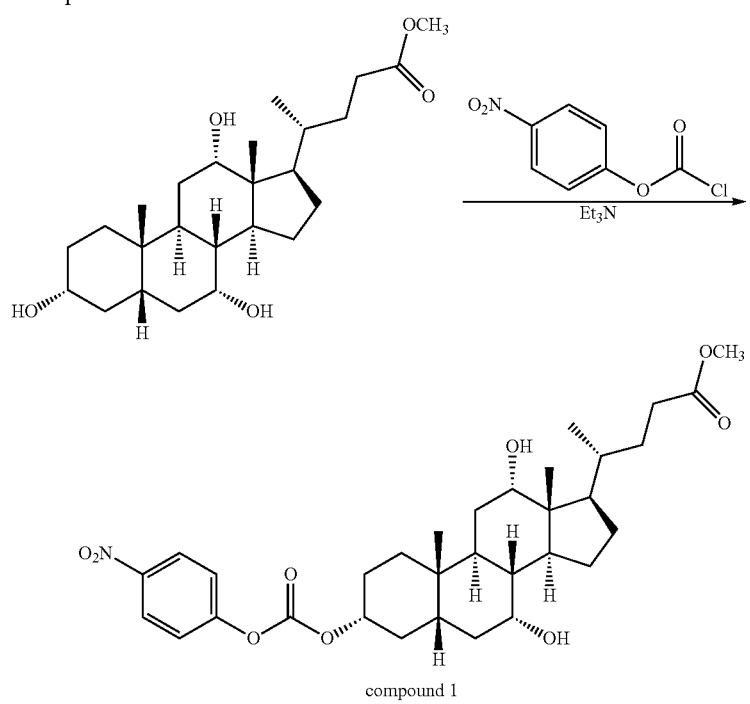
Step 3:
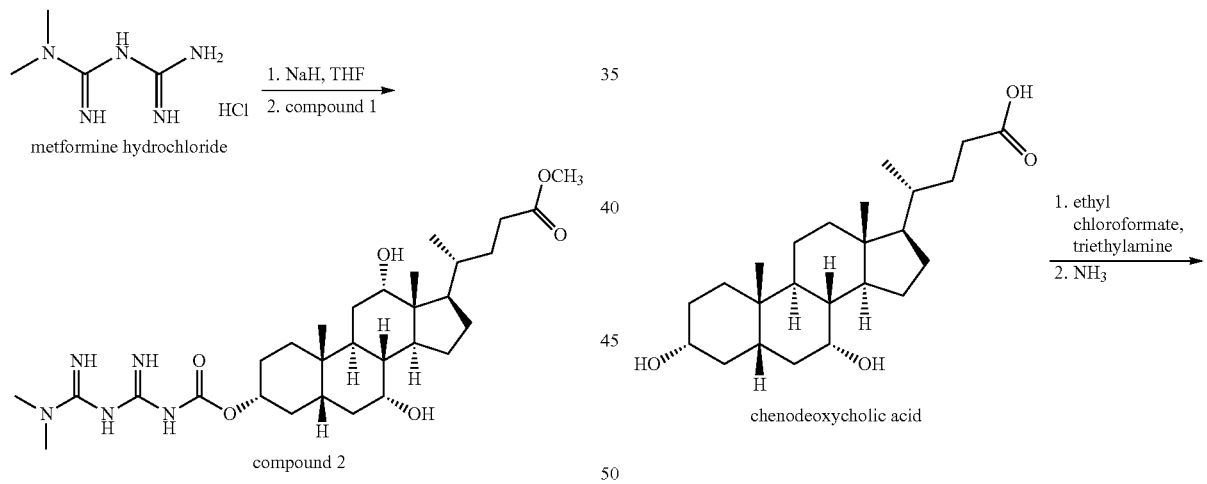
In another example of the invention, the compound is of the structure of compound 5 below:
The scheme for synthesizing compound 5 is given below:
Step 1:
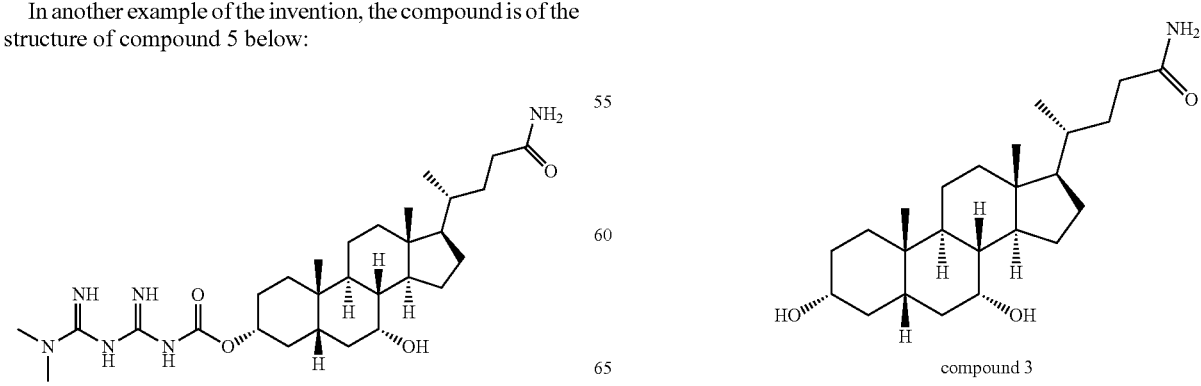

Step 2:

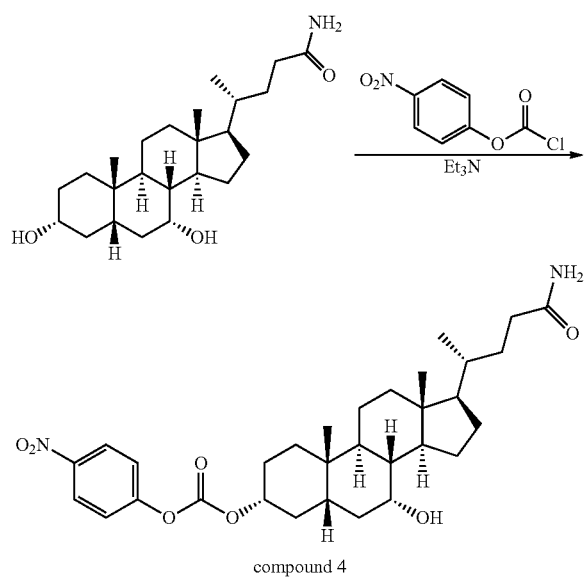

compound 4

Step 3:

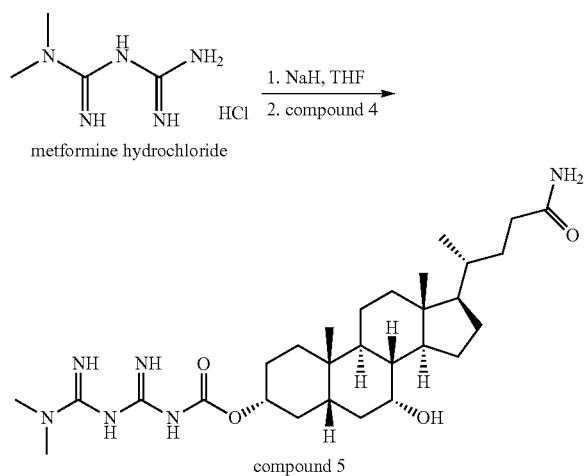

compound 5

The invention also provides a pharmaceutical composition comprising a therapeutically effective amount of the compound of the invention, and one or more pharmaceutically acceptable carriers, diluents or excipients.

The term "pharmaceutically acceptable salt" as used herein refers to any non-toxic salt of the compound of the present invention. Typically, the pharmaceutically acceptable salts of the present invention may include acid addition salts. Representative salts include acetate, benzenesulfonate, benzoate, bicarbonate, bisulfate, bitartrate, borate, bromide, calcium edetate, camsylate, carbonate, chloride, clavulanate, citrate, hydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. In one particular example of the invention, the pharmaceutically acceptable salt is hydrochloride.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation.

The term "therapeutically effective amount" as used herein refers to an amount of a drug or pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of the compound of the invention may be formulated as a pharmaceutical composition for administration. Accordingly, the invention further provides a pharmaceutical composition comprising a therapeutically effective amount of the compound of the invention and one or more pharmaceutically acceptable carriers, diluents, or excipients. The carrier(s), diluent(s) or excipient(s) must be acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

A therapeutically effective amount of a compound of the present invention will depend upon a number of factors. For example, the age and weight of the animal, the precise condition requiring treatment and its severity, the nature of the formulation, and the route of administration are all factors to be considered. For example, a therapeutically effective amount of the compound of the invention for the treatment of humans suffering from type-2 diabetes, generally, should be about 10 to about 2000 mg/kg (such as about 30-50 mg/kg) per dose, one or several doses a day. For example, the dose may be 1500 mg twice a day or 2550 mg once a day.

According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

In one example of the invention, the pharmaceutical composition for oral administration may be presented as discrete units such as capsules or tablets; powders or granules; solutions or suspensions, and the like. In one particular example, the pharmaceutical composition is in the form of tablets.

The efficacy of the compound of the invention (such as Compound 2) in lowering blood glucose in animals was evaluated (see Example 3). It was shown that the compound of the invention (compound 2) improved hyperglycemia primarily through the suppression of hepatic glucose production (hepatic glyconeogenesis), in terms of the efficacy in lowering blood glucose in animals. In addition, the compound of the invention is eliminated via the hepatic route, instead of the renal route because of the moiety of steroid (or bile salt). Therefore, the compound of the invention is confirmed to be effective in the treatment of diabetes, particularly type-2 diabetes, especially when accompanying obesity and insulin resistance.

The present invention will now be described more specifically with reference to the following examples, which are provided for the purpose of demonstration rather than limitation.

Example 1

Preparation of Compound 2

Step 1:

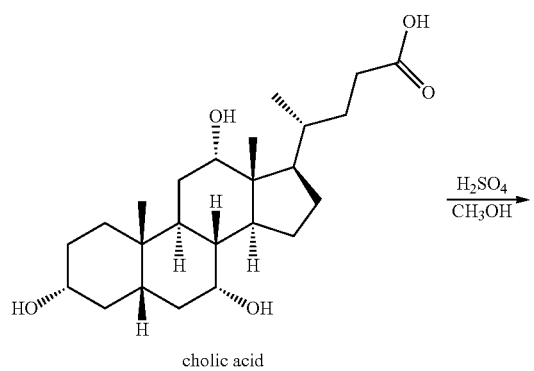

Methyl cholate was prepared from cholic acid using the method of J. Med. Chem., 2004, Vol. 47, No. 17, 4213-4230.

Step 2:

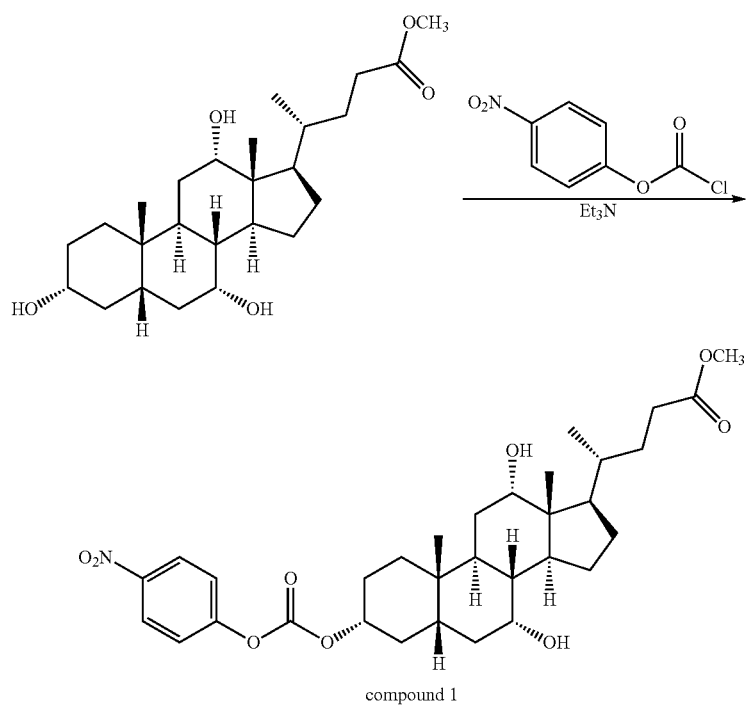

To a solution of cholic acid methyl ester (2.0 g, 4.7 mmol) stirring in pyridine (5 mL) at 0° C. was added 4-nitrophenyl-chloroformate (1.4 g, 7.1 mmol). The mixture was stirred at 0° C. for 30 min and at room temperature for one hour. The reaction mixture was partitioned between ethyl acetate (50 mL) and 1 N HCl (50 mL). The aqueous layer was extracted with ethyl acetate (3×30 mL). The combined organic layers were washed with brine (50 mL), dried over MgSO$_4$, and concentrated in vacuum to afford crude compound 1.

Step 3:

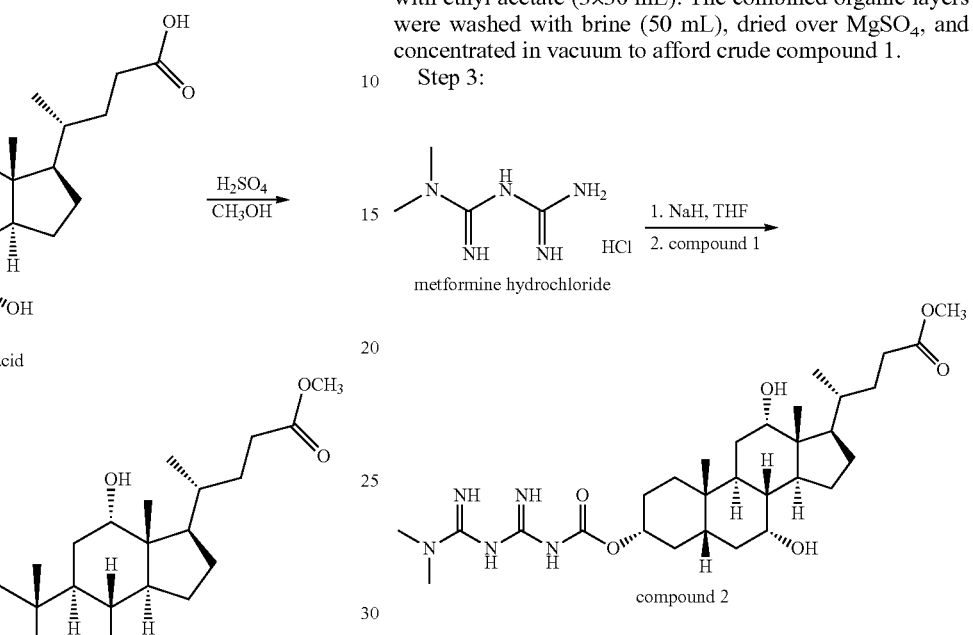

Figure 2:
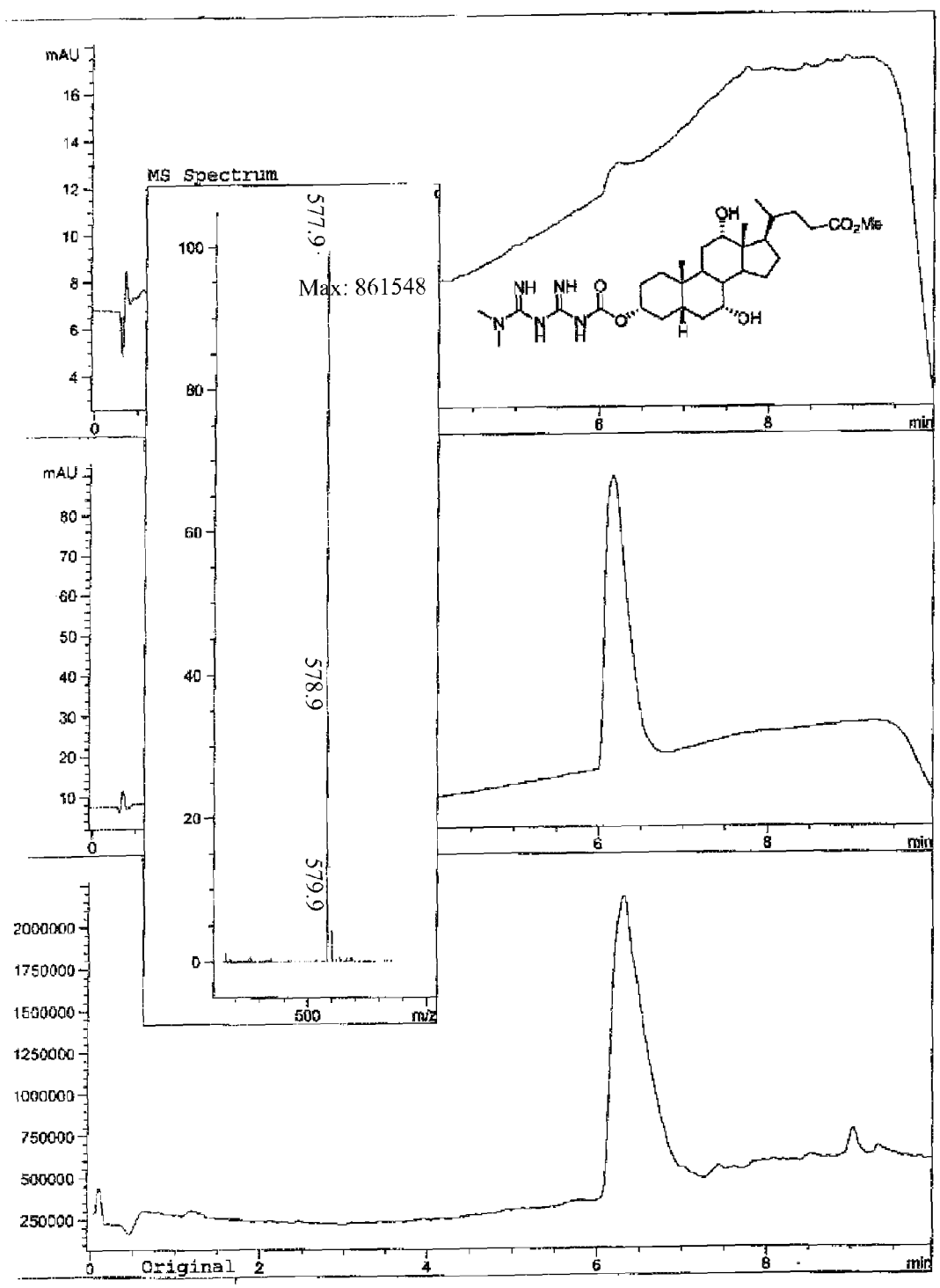
FIG. 2 provides the ESI-MS profile of Compound 2.

To a suspension of sodium hydride (2.4 g, 0.1 mmol) in THF was added metformine hydrochloride (18.5 g, 0.11 mmol) slowly at 0° C. After stifling at the same temperature for 30 min, the solution of compound 1 in THF was added dropwise. The reaction mixture was stirred further at ambient temperature for one hour. After the reaction was completed, the mixture was partitioned between ethyl acetate (50 mL)

and water (50 mL). The organic layer was washed with brine, dried over MgSO$_4$, and concentrated in vacuum to afford compound 2 [$^1$H NMR (CD$_3$OD, 300 Hz) 0.72 (s, 3H), 0.85-2.15 (m, 26H), 2.18-2.60 (m, 4H), 3.07 (s, 6H), 3.65 (s, 3H), 3.81 (m, 1H), 3.96 (s, 1H), 4.57 (m, 1H); ESI-MS m/z 577.9 (M+H$^+$), FIG. 1]. The compound 2 was also identified by the ESI-MS profile, see FIG. 2.

Example 2

Preparation of Compound 5

Step 1:

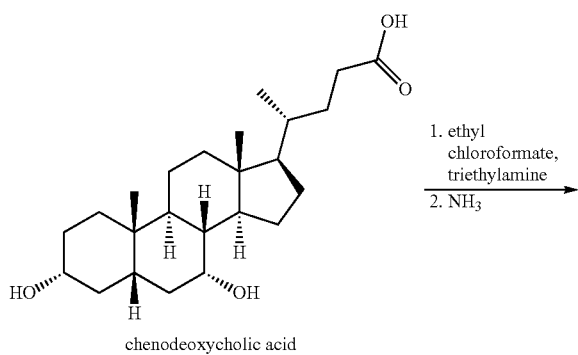

chenodeoxycholic acid 1. ethyl chloroformate, triethylamine
2. NH$_3$ compound 3

To a solution of ethyl chenodeoxycholic acid (3.93 g, 10.0 mmol) and triethylamine (2.0 ml, 14.4 mmol) in anhydrous tetrahydrofuran (25 mL) was added ethyl chloroformate (1.0 ml, 10.5 mmol) dropwise at 0° C. with stifling. The suspension was further stirred at room temperature for half an hour. A stream of ammonia was bubbled into the suspension using a gas-dispersion tube for 10 min and then the resulting mixture was concentrated under reduced pressure. The residue was partitioned between dichloromethane and water. The organic layer was washed with brine, dried over MgSO$_4$, and concentrated to afford compound 3.

Step 2:

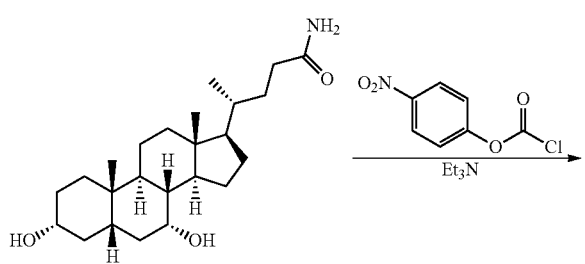

Et$_3$N compound 4

To a solution of compound 3 (2.00 g, 5.11 mmol) stirring in pyridine (5 mL) at 0° C. was added 4-nitrophenylchloroformate (1.55 g, 7.67 mmol). The mixture was stirred at 0° C. for 30 min and at room temperature for one hour. The reaction mixture was partitioned between ethyl acetate (50 mL) and 1 N HCl (50 mL). The aqueous layer was extracted with ethyl acetate (3×30 mL). The combined organic layers were washed with brine (50 mL), dried over MgSO$_4$, and concentrated in vacuum to afford crude compound 4.

Step 3:

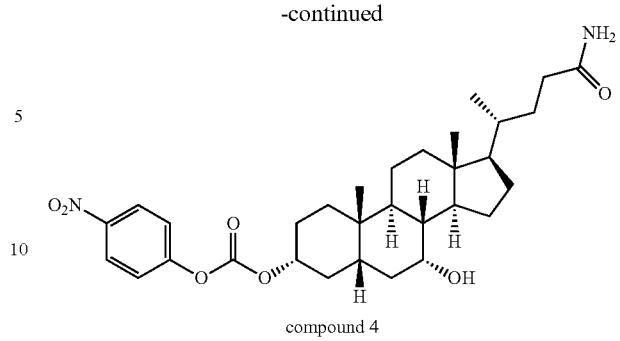

metformine hydrochloride

1. NaH, THF
2. compound 4 compound 5

Figure 3:
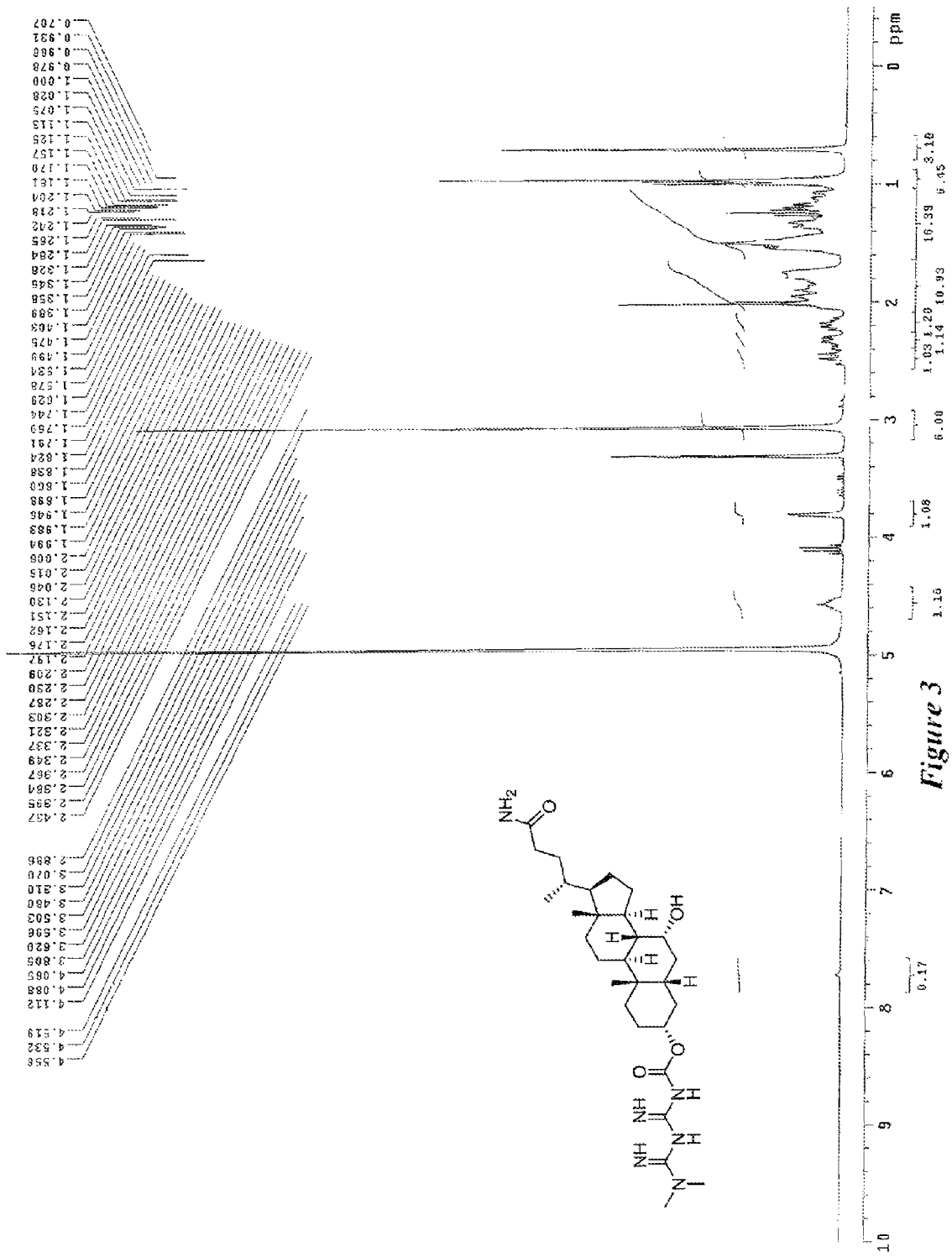
FIG. 3 provides the of the $^1$H NMR (CD$_3$OD, 300 Hz) profile of Compound 5, which is another example of the invention.
Figure 4:
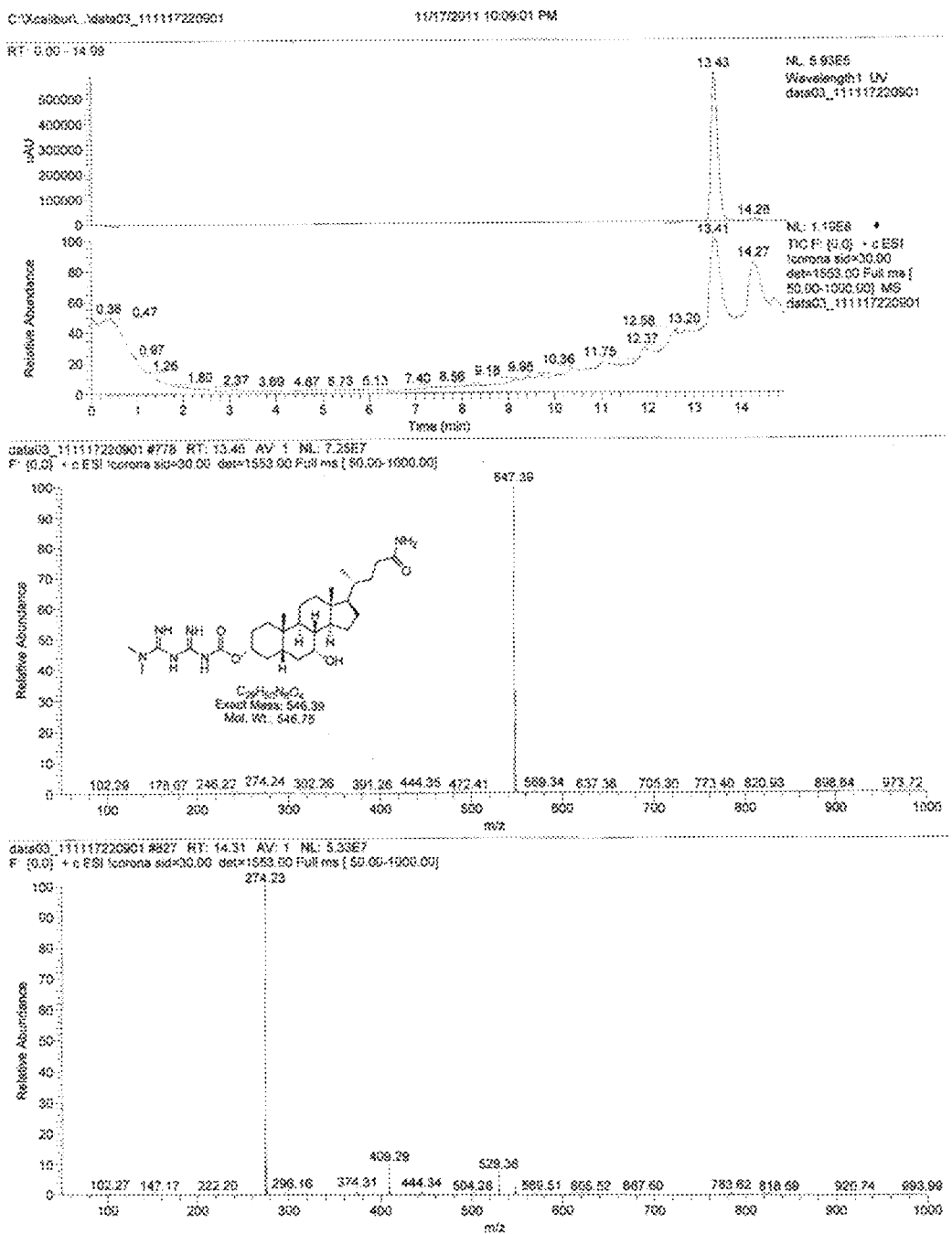
FIG. 4 provides the ESI-MS profile of Compound 5.

To a suspension of sodium hydride (2.4 g, 0.1 mmol) in THF was added metformine hydrochloride (18.5 g, 0.11 mmol) slowly at 0° C. After stifling at the same temperature for 30 min, the solution of compound 4 (0.06 g, 0.10 mmol) in THF was added dropwise. The reaction mixture was stirred further at ambient temperature for one hour. After the reaction was completed, the mixture was partitioned between ethyl acetate (50 mL) and water (50 mL). The organic layer was washed with brine, dried over MgSO$_4$, and concentrated in vacuum to afford compound 5 [$^1$H NMR (CD$_3$OD, 300 Hz) 0.71 (s, 3H), 0.85-2.10 (m, 29H), 2.10-2.60 (m, 3H), 3.07 (s, 6H), 3.65 (s, 3H), 3.81 (s, 1H), 4.53 (m, 1H); ESI-MS m/z 547.3 (M+H$^+$), see FIG. 3]. The compound 5 was also identified by the ESI-MS profile, see FIG. 4.

Example 3

Animal Test

Approximately 7-9-week-old ICR mouse were purchased from BioLASCO Taiwan Co., Ltd (Taipei, Taiwan). The animals were randomly divided into 4 groups as shown in the following Table 1:

TABLE 1

| No. | Group | Test Compound | Dosage (mg/kg) | Concentration (mg/mL) | Dose Volume (mL/kg) |
|---|---|---|---|---|---|
| 1 | Vehicle control (Negative control) | Solvent (5% DMSO in WFI) | 0 | 0 | 10 |
| 2 | Active control | Metformin Hydrochloride | 150 | 15 | 10 |
| 3 | Test 1 | Compound 2 | 525 | 52.5 | 10 |
| 4 | Test 2 | Compound 2 | 1050 | 105 | 10 |

Linear analysis of the glucose monitoring system: eight concentrations (0, 50, 100, 200, 300, 400, 500, 600 mg/dL) of glucose solution were determined duplicate. The animals were fasted approximately 4 hours before dosing. Then, the animals were administered with the test compounds via oral gavage. After 30 minutes of the test compound dosed, the animals were administered with 1.5 g/kg glucose solution (Concentration: 0.15 g/mL, Dose volume: 10 mL/kg) via oral gavage. The blood glucose was determined before the test compound dosing, before glucose dosing, and after glucose dosing in 5, 15, 20, 25, 30, 40 and 50 minutes. The results were given in Table 2 and FIG. 5.

| Group | Test Compound | Means* at 20 min. | Significance ($p < 0.05$) |
|---|---|---|---|
| Vehicle control (Negative control) | Solvent (5% DMSO in WFI) | 358.0 | A |
| Active control | Metformin Hydrochloride | 125.4 | B |
| Test 1 | Compound 2 | 225.8 | B |
| Test 2 | Compound 2 | 225.8 | B |

*mean: Mean value of glucose level at 20 min. minus glucose level at time zero (before glucose dosing.

Figure 5:
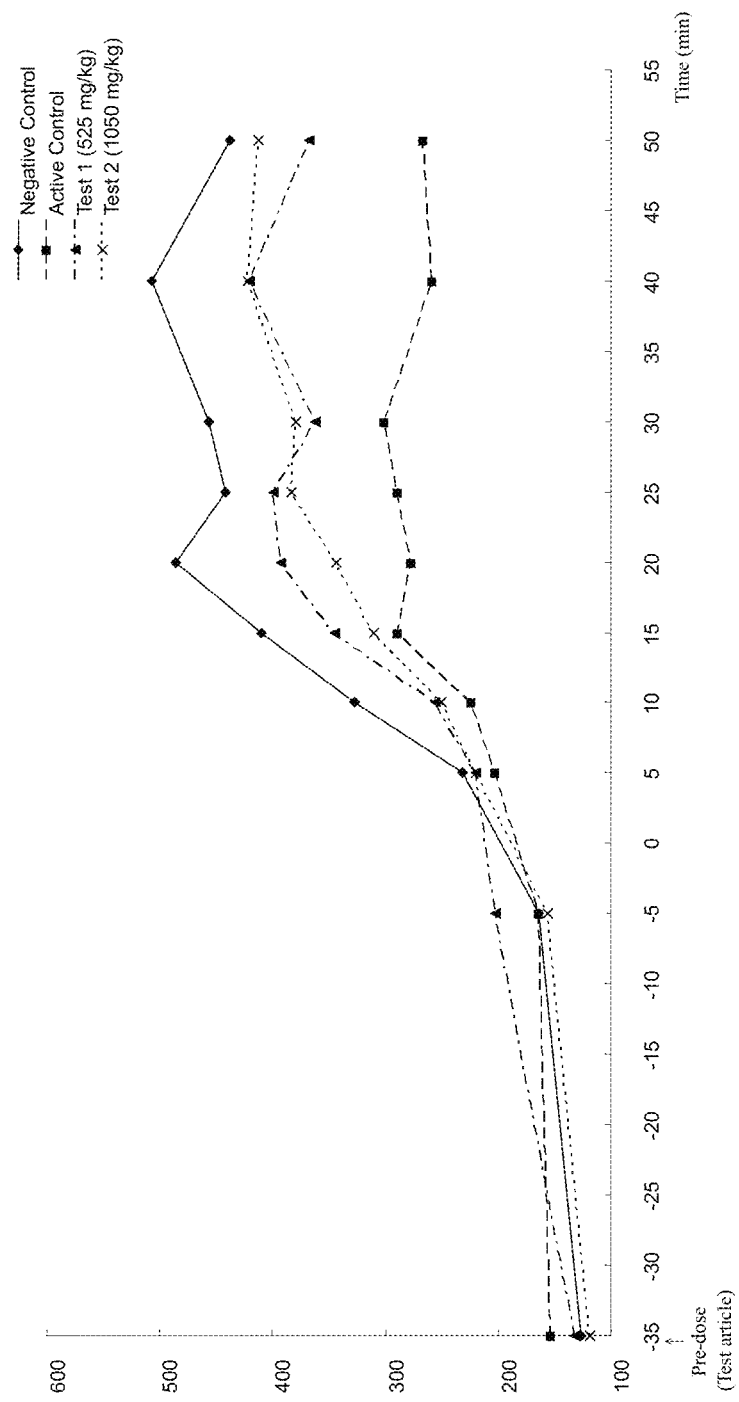
FIG. 5 shows the results of the glucose level of the animals administered with the Vehicle (Negative group), Metformin Hydrochloride (Active group) at the dose of 150 mg/kg or Compound 2 (the compound according to the invention) at the dose of 525 and 1050 mg/kg respectively; wherein the responses of the groups after dosing were significantly different from the negative group.

As shown in FIG. 5, the blood glucose level was lowered when the animals were administered with Compound 2 (the compound according to the invention) or Metformin Hydrochloride (the active control), as compared with the Vehicle group (negative group) during the test period. After 20 min., the glucose level reached plateau. It appeared that Compound 2 (the compound according to the invention) provided the efficacy in lowering blood glucose, like Metformin Hydrocholoride; as shown in Table 2, the responses of the groups administered with Metformin, Compound 2 (the compound of the invention) was significantly different from that of the vehicle control (negative group), p<0.05.

Statistical Analysis

The results were expressed as means and the statistical significance was evaluated by analysis of variance (ANOVA) followed by least significance difference post hoc test. A level of p<0.05 was considered statistically significant.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A compound having the structure of Formula Ia or Ib

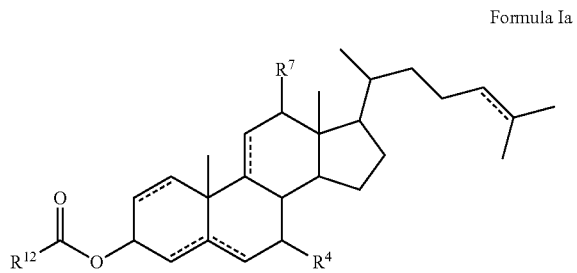

Formula Ia

Formula Ib wherein $R^4$ and $R^7$ are independently hydrogen, hydroxyl, methoxyl, ethoxyl, =O, —O-acetyl, or —O-benzoyl;

$R^{17}$ is hydroxyl, methoxyl, ethoxyl, or one amino group selected from those of the following formulas:

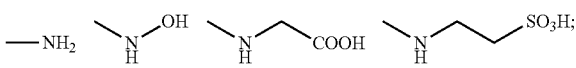

and $R^{12}$ is a guanide or biguanide having the following formula:

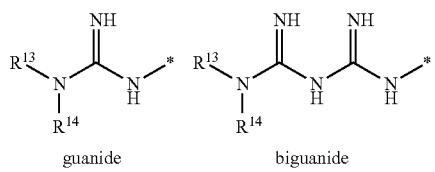

guanide     biguanide wherein $R^{13}$ and $R^{14}$ are independently selected from hydrogen, methyl, n-butyl, or phenethyl.

2. The compound of claim 1, wherein $R^{12}$ is a biguanide.

3. The compound of claim 1, wherein each of $R^{13}$ and $R^{14}$ is hydrogen.

4. The compound of claim 1, which is

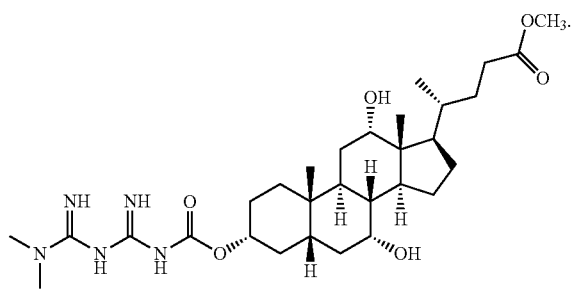

5. The compound of claim 1, which is

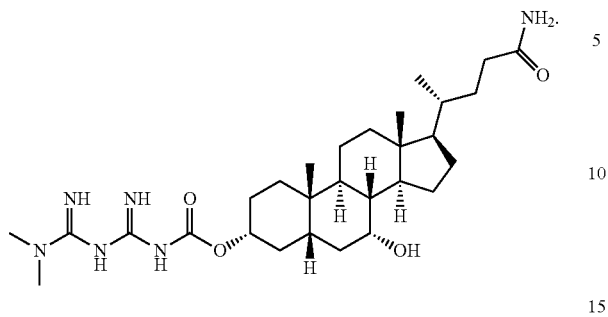

6. A pharmaceutical composition comprising the compound of claim 1, and one or more pharmaceutically acceptable carriers, diluents, or excipients.

7. A pharmaceutical composition of claim 6, wherein the compound is the compound of claim 1.

8. A pharmaceutical composition of claim 6, wherein the compound is the compound of claim 4.

9. A pharmaceutical composition of claim 6, wherein the compound is the compound of claim 5.

10. The pharmaceutical composition of claim 6, which is for the treatment of diabetes.

11. The pharmaceutical composition of claim 10, wherein the diabetes is type-2 diabetes.

* * * * *